United States Patent
Yamaya

(10) Patent No.: US 10,136,798 B2
(45) Date of Patent: Nov. 27, 2018

(54) ENDOSCOPIC SYSTEM

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/487,535

(22) Filed: Apr. 14, 2017

(65) Prior Publication Data
US 2017/0215705 A1   Aug. 3, 2017

Related U.S. Application Data

(63) Continuation of application No. PCT/JP2015/080772, filed on Oct. 30, 2015.

(30) Foreign Application Priority Data

Dec. 10, 2014   (JP) ................. 2014-250216

(51) Int. Cl.
*A61B 1/00* (2006.01)
*A61B 1/018* (2006.01)
(Continued)

(52) U.S. Cl.
CPC ...... *A61B 1/00133* (2013.01); *A61B 1/00066* (2013.01); *A61B 1/00071* (2013.01);
(Continued)

(58) Field of Classification Search
CPC ............ A61B 1/00133; A61B 1/00071; A61B 1/00066; A61B 1/00128; A61B 1/018; A61B 18/16; A61B 18/1482
See application file for complete search history.

(56) References Cited

FOREIGN PATENT DOCUMENTS

| JP | H07-059730 A | 3/1995 |
|----|--------------|--------|
| JP | 2003-079564 A | 3/2003 |

(Continued)

OTHER PUBLICATIONS

English translation of International Preliminary Report on Patentability dated Jun. 22, 2017 together with the Written Opinion received in related International Application No. PCT/JP2015/080772.

(Continued)

*Primary Examiner* — Timothy J Neal
(74) *Attorney, Agent, or Firm* — Scully, Scott, Murphy & Presser, P.C.

(57) ABSTRACT

An endoscope including an insertion portion which is provided with a channel to insert a treatment instrument therethrough, an operation portion which is operated the insertion portion, and an operation lever which holds and moves the treatment instrument to transmit force of the operation to the treatment instrument; and an assistant instrument which assists the movement of the treatment instrument, the assistant instrument comprising a flexible tube in which the insertion path is formed to insert the treatment instrument, a coupling portion which is formed so that the channel is coupled to the insertion path, and a holding portion which is attached to the vicinity of the other end of the flexible tube and which holds the operation portion so that the other end of the flexible tube faces toward the side where the operation lever is disposed.

6 Claims, 6 Drawing Sheets

(51) Int. Cl.
*A61B 18/14* (2006.01)
*A61B 1/015* (2006.01)
*A61B 18/12* (2006.01)
*A61B 18/16* (2006.01)
*A61B 18/00* (2006.01)

(52) U.S. Cl.
CPC ...... *A61B 1/00087* (2013.01); *A61B 1/00091* (2013.01); *A61B 1/00096* (2013.01); *A61B 1/00121* (2013.01); *A61B 1/00128* (2013.01); *A61B 1/015* (2013.01); *A61B 1/018* (2013.01); *A61B 18/1482* (2013.01); *A61B 18/12* (2013.01); *A61B 18/16* (2013.01); *A61B 2018/00601* (2013.01)

(56) References Cited

FOREIGN PATENT DOCUMENTS

| | | |
|---|---|---|
| JP | 2005-058749 A | 3/2005 |
| JP | 2006-204745 A | 8/2006 |
| JP | 2013-198673 A | 10/2013 |

OTHER PUBLICATIONS

International Search Report dated Dec. 15, 2015 issued in PCT/JP2015/080772.

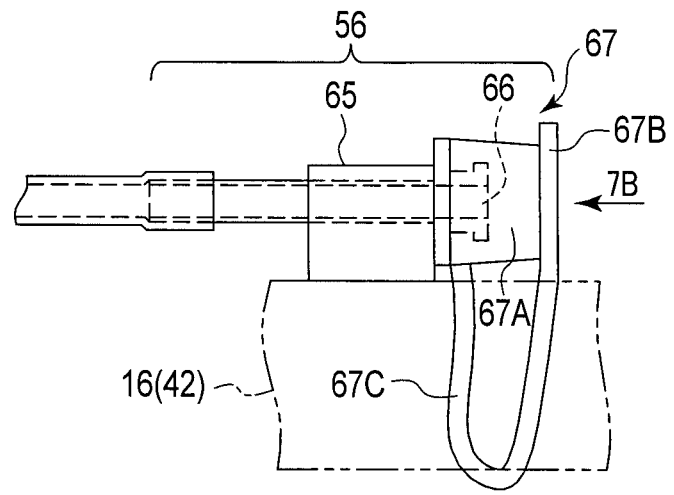
F I G. 7A
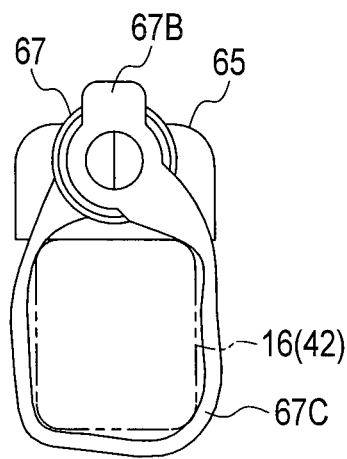
F I G. 7B

ENDOSCOPIC SYSTEM

CROSS-REFERENCE TO RELATED APPLICATIONS

This is a Continuation Application of PCT Application No. PCT/JP2015/80772, filed Oct. 30, 2015, which was published under PCT Article 21(2) in Japanese.

This application is based upon and claims the benefit of priority from prior the Japanese Patent Application No. 2014-250216, filed Dec. 10, 2014 the entire contents of which are incorporated herein by references.

BACKGROUND OF THE INVENTION

1. Field of the Invention

This invention relates to an endoscopic system having an assistant instrument which assists the operation of a treatment instrument.

2. Description of the Related Art

There has been an endoscopic treatment instrument which is used together with an endoscope and which conducts various treatments for a treatment target. The endoscopic treatment instrument described in PATENT LITERATURE 1: Jpn. Pat. Appln. KOKAI Publication No. 2006-204745 comprises a tubular sheath portion, a long treatment instrument body attached to be able to move back and forth in the sheath portion, and an attachment portion to attach the sheath portion to the endoscope. The sheath portion has a flexible sheath which is inserted into a body cavity, and a proximal support portion which supports the flexible sheath. This endoscopic treatment instrument enables a treatment to collect, for example, gallstones by the insertion of the treatment instrument body and the flexible sheath into the body cavity via an endoscope insertion portion.

BRIEF SUMMARY OF THE INVENTION

According to an embodiment of the present invention, there is provided an endoscopic system comprising: an endoscope including an insertion portion which is inserted into a body cavity and which is provided with a channel to insert a treatment instrument therethrough, an operation portion which is connected to the insertion portion and which operates the insertion portion, and an operation lever which is provided in the operation portion and which holds and moves the treatment instrument to transmit force of the operation to the treatment instrument; and an assistant instrument which assists the movement of the treatment instrument, the assistant instrument comprising a flexible tube in which the insertion path is formed to insert the treatment instrument that is inserted into the channel of the insertion portion, a coupling portion which is connected to one end of the flexible tube and which is formed so that the channel is coupled to the insertion path, and a holding portion which is attached to the vicinity of the other end of the flexible tube and which holds the operation portion so that the other end of the flexible tube faces toward the side where the operation lever is disposed.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 7A is a schematic diagram showing, in a magnified form, a part of the treatment instrument back-and-forth movement assistant instrument and the operation portion of the endoscope according to the endoscopic system of the fourth embodiment; and FIG. 7B is a schematic diagram showing a state where the treatment instrument back-and-forth movement assistant instrument and the operation portion shown in FIG. 7A are seen from the direction of an arrow 7B.

DETAILED DESCRIPTION OF THE PREFERRED EMBODIMENT

Figure 1A:
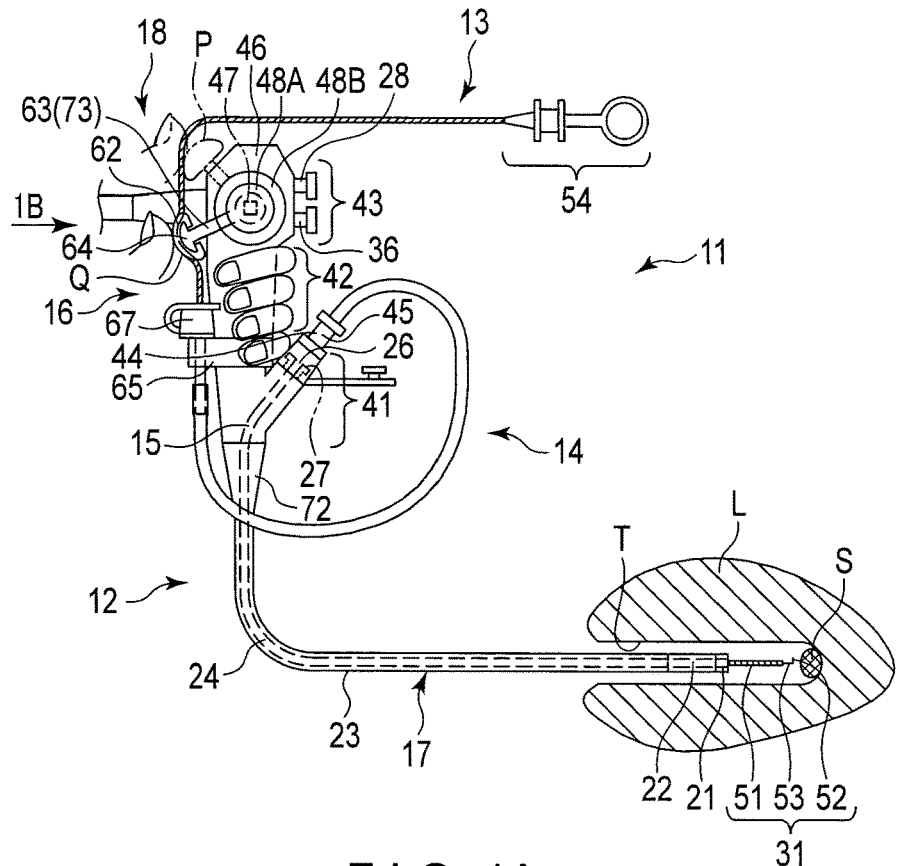
FIG. 1A is a schematic diagram of the overall configuration of an endoscopic system according to a first embodiment.

Hereinafter, embodiments of this invention will be described with reference to the drawings.

An endoscopic system according to the first embodiment is described by use of FIG. 1A to FIG. 4C. An endoscopic system 11 (endoscopic apparatus) according to this embodiment has an endoscope 12, a treatment instrument 13, and an assistant instrument 14 which assists the movement of the treatment instrument. The treatment instrument 13 is movable relative to a later-described treatment instrument insertion channel 15 of the endoscope 12. The assistant instrument 14 which assists the movement of the treatment instrument is removably held to an operation portion 16 of the endoscope 12. The assistant instrument 14 which assists the movement of the treatment instrument is used to assist the movement (back-and-forth movement and rotation) of the treatment instrument 13 relative to the treatment instrument insertion channel 15. That is, the assistant instrument 14 which assists the movement of the treatment instrument assists the movement of the treatment instrument 13 which has been extended from one end of the assistant instrument 14 relative to the endoscope 12 by a surgeon.

Figure 1B:
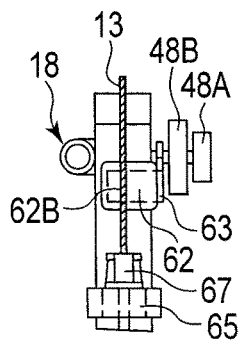
FIG. 1B is a schematic diagram showing the vicinity of an operation portion of the endoscopic system in FIG. 1A from an arrow 1B direction.

The structure of the endoscope 12 is briefly described by use of FIG. 1A and FIG. 1B. A publicly known suitable endoscope 12 having the treatment instrument insertion channel 15 has only to be used. As shown in FIG. 1A and FIG. 1B, the endoscope 12 has an elongated insertion portion 17 which is inserted into a body cavity (lumen), the operation portion 16 provided to be connected to the proximal end of this insertion portion 17, and a universal cord 18 extended from the side portion of this operation portion 16.

The insertion portion 17 has, from the distal side to the proximal side in order, a rigid distal configuration portion 21, a curving portion 22 having a freely curvable curving tube in which unshown curving pieces are connected in contact with one another, and a flexible tubular portion 23 which flexibly bends due to external force.

A channel tube 24 (treatment instrument insertion tube) that constitutes the treatment instrument insertion channel 15 is provided inside the insertion portion 17. The distal end of the channel tube 24 is connected to a later-described distal side opening 25 of the distal configuration portion 21 (see FIG. 2). Preferably, the channel tube 24 is branched, for example, inside the operation portion 16 as is publicly known. A first proximal end of the channel tube 24 is connected to a hand-side opening 26 (first connection mouth ring 27). A second proximal end (not shown) of the channel tube 24 is connected to a later-described suction button 28 of a suction mechanism. In the treatment instrument insertion channel 15, the space between the distal side opening 25 of the distal configuration portion 21 and a branch portion of the channel tube 24 is formed as an insertion path through which an insertion section 31 of the treatment instrument 13 is inserted, and also formed as a suction pipe. The suction mechanism is not necessarily required in the endoscope 12 according to this embodiment.

Figure 2:
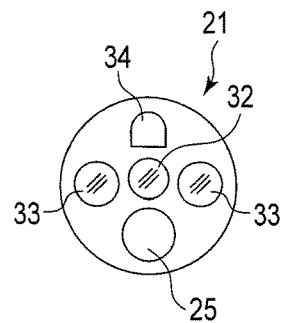
FIG. 2 is a schematic diagram showing a distal face of a distal configuration portion of an insertion portion of an endoscope in the endoscopic system according to the first embodiment.

As shown in FIG. 2, the distal configuration portion 21 has, in its distal face, the distal side opening 25, an observation window 32, preferably two illumination windows 33 (one illumination window 33 is also possible), and a nozzle 34. As shown in FIG. 1A and FIG. 1B, the distal side opening 25 is coupled to and is thus in communication with the distal end of the channel tube 24 and forms the distal end of the treatment instrument insertion channel 15. The observation window 32 constitutes the distal end of an observation optical system to observe an observation part. The illumination windows 33 constitute the distal end of an illumination optical system to illuminate the observation part. The nozzle 34 can discharge gases and liquids from an unshown discharge opening directed toward the observation window 32. A later-described air/water supply button 36 operates the discharge of the gases and liquids.

As shown in FIG. 1A and FIG. 1B, the operation portion 16 has, from its distal side to proximal side in order, a treatment instrument introduction portion 41, a grasping portion 42, and a operation portion body 43. It is appropriate that the treatment instrument introduction portion 41, the grasping portion 42, and the operation portion body 43 be integrally formed.

The treatment instrument introduction portion 41 has the hand-side opening 26 (first connection mouth ring 27) to which the first proximal end of the channel tube 24 is connected. An assistant instrument plug 44 is attached to the hand-side opening 26 of the treatment instrument introduction portion 41.

The assistant instrument plug 44 has a valve structure which inhibits the leakage of the liquid flowing to the proximal side through the channel tube 24 to the outside of the endoscope 12 in a state where the later-described insertion section 31 of the treatment instrument 13 and a later-described coupling portion 45 of the assistant instrument 14 which assists the movement of the treatment instrument are inserted through the assistant instrument plug 44. The assistant instrument plug 44 can also serve as a brake which prevents unintentional movement of the treatment instrument 13. The assistant instrument plug 44 similar to a publicly known forceps plug may be used.

The grasping portion 42 is a part which is grasped with one hand, for example, the left hand by the surgeon. The operation portion body 43 can operate the curving of the curving portion 22. The universal cord 18 is extended from the side portion of the operation portion body 43.

The operation portion body 43 has a case 46, a shaft 47 protruding from the case 46, curving operation knobs 48A and 48B fixed to the shaft 47, the air/water supply button 36, and the suction button 28. The curving operation knobs 48A and 48B can remotely operate the curving of the curving portion 22. Generally, the surgeon operates the curving operation knobs 48A and 48B with, for example, the thumb of the left hand while holding the grasping portion 42 in the palm of the left hand. The curving operation knobs 48A and 48B are an example of a second operation lever.

Another example of the second operation lever is a raising base operation lever which operates a raising base provided in the distal configuration portion 21. The raising base operation lever is provided in, for example, the operation portion 16. By operating the raising base operation lever, the surgeon can operate the raising base to stand (raise) the treatment instrument 13 which is passed through the treatment instrument insertion channel 15, in a direction that intersects with the axial direction of the insertion portion 17 of the endoscope 12. An air/water supply mechanism including the air/water supply button 36 and the suction mechanism including the suction button 28 are publicly known and are therefore not described here.

The treatment instrument 13 has the insertion section 31 which can be inserted through the treatment instrument insertion channel 15 of the endoscope 12, and a base portion 54 (hand-side operation portion) which is provided at the proximal end of the insertion section 31. The insertion section 31 is formed longer than the entire length of the treatment instrument insertion channel 15, and may be, for example, several times longer. The distal end of the insertion section 31 can be put in and out of the distal configuration portion 21 of the insertion portion 17 through the treatment instrument insertion channel 15 of the endoscope 12. The insertion section 31 generally has a diameter of, for example, 1 to 2 mm.

The insertion section 31 has a sheath 51, and a wire 53 having an end effector 52 at the distal end thereof. The sheath 51 may be formed by a mere insulating resinous tube, or may be, for example, a coil sheath, which is selected depending on the end effector 52. The wire 53 is flexible.

The end effector 52 having a suitable shape such as a substantially L-shape, a snare shape, or a basket shape can be used. The end effector 52 can conduct a suitable treatment using high-frequency energy for a living tissue between the end effector 52 and an unshown return electrode which is attached to a patient.

The base portion 54 has a publicly known slider mechanism. The wire 53 can move along its axial direction relative to the sheath 51 by the operation of the slider mechanism in the base portion 54. Thus, the wire 53 can be moved back and forth along the axial direction of the insertion section 31 relative to the sheath 51 by the slider mechanism. The surgeon can turn or rotate the insertion section 31, that is, the sheath 51 and the wire 53 together around the axis of the insertion section 31 by holding the same.

The assistant instrument 14 which is used to move the treatment instrument 13 back and forth relative to the treatment instrument insertion channel 15 of the endoscope 12 is described by use of FIG. 1A and FIG. 1B, and FIG. 3A and FIG. 3B. The assistant instrument 14 which assists the movement of the treatment instrument has a long flexible tube 55, the coupling portion 45 which allows the proximal (connection end) side of the flexible tube 55 to be attached to and detached from the hand-side opening 26 of the endoscope 12, and a holding portion 56 which holds the outside of the operation portion 16 (the grasping portion 42) of the endoscope 12 on the distal (movement end) side of the flexible tube 55.

A tube which is easy to bend and which is difficult to break and which provides satisfactory slipping efficiency for the insertion section 31 of the treatment instrument 13 is preferably used as the flexible tube 55. For example, the following tubes are used as the flexible tube 55: a fluorine-based resin tube, a fluorine-based resin tube in which braids are put to increase bending resistance, or a tube in which an insertion path 58 within the flexible tube 55 is coated with a fluorine-based resin to increase the back-and-forth movability of a braided urethane-based resin tube along the axial direction of the insertion section 31 of the treatment instrument 13. The entire length of the flexible tube 55 is formed to be shorter than the entire length of the insertion section 31 of the treatment instrument 13, but is preferably about 400 mm for use.

Figure 3A:
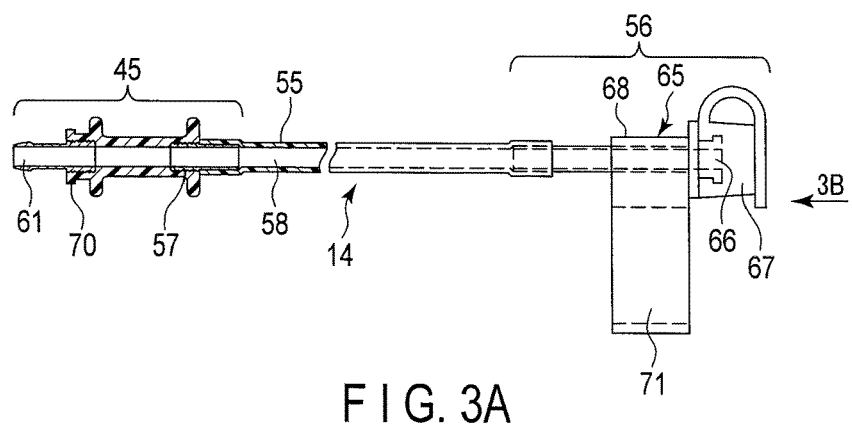
FIG. 3A is a schematic diagram showing a treatment instrument back-and-forth movement assistant instrument of the endoscopic system according to the first embodiment.
Figure 3B:
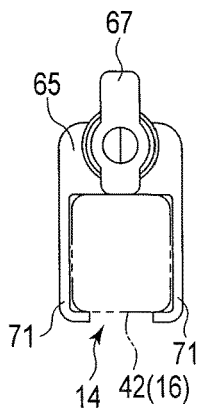
FIG. 3B is a schematic diagram showing a state where a holding portion of the treatment instrument back-and-forth movement assistant instrument shown in FIG. 3A is seen from an arrow 3B direction.

As shown in FIG. 3A and FIG. 3B, the flexible tube 55 has caps at its distal end and the other end, respectively. The distal side cap is connected to the holding portion 56. A proximal side cap 57 is connected to the coupling portion 45.

The assistant instrument 14 which assists the movement of the treatment instrument forms the insertion path 58 by the flexible tube 55, the coupling portion 45, and the holding portion 56. The insertion path 58 is formed over the entire length of the assistant instrument 14 which assists the movement of the treatment instrument, and the insertion section 31 of the treatment instrument 13 is inserted through the insertion path 58.

The coupling portion 45 has a second connection mouth ring 61 having a proximal side opening end of the insertion path 58. The second connection mouth ring 61 is coupled to the assistant instrument plug 44 while the valve structure of the assistant instrument plug 44 is kept open at the proximal side opening end. That is, in the present embodiment, the second connection mouth ring 61 of the coupling portion 45 and a neighboring protruding portion 70 are inserted and fitted into a recessed portion (not shown) within the assistant instrument plug 44 which is attached to the hand-side opening 26 of the endoscope 12 and which is made of an elastic member. Thus, the coupling portion 45 of the assistant instrument 14 which assists the movement of the treatment instrument communicates with the treatment instrument insertion channel 15 of the endoscope 12 via the assistant instrument plug 44 of the hand-side opening 26 (first connection mouth ring 27) of the endoscope 12, and brings the channel and the insertion path 58 into communication with each other. The coupling portion 45 of the assistant instrument 14 which assists the movement of the treatment instrument is attachable to and detachable from the assistant instrument plug 44 attached to the hand-side opening 26 of the endoscope 12.

The method of connecting the coupling portion 45 to the hand-side opening 26 of the endoscope 12 is not limited to the example according to the present embodiment. The coupling portion 45 may be directly fixed to be attachable to and detachable from the hand-side opening 26 and to prevent liquid leakage without the use of the assistant instrument plug 44. Specifically, for example, the coupling portion 45 can be formed by an elastic member such as silicone rubber instead of the resin material, and directly and watertightly fixed to the hand-side opening 26 of the endoscope 12. The coupling portion 45 may be omitted so that the proximal side of the flexible tube 55 is directly inserted into the treatment instrument insertion channel 15 to fix the assistant instrument 14 which assists the movement of the treatment instrument and to fix the endoscope 12.

As shown in FIG. 1A and FIG. 1B, the holding portion 56 is provided in the vicinity of a finger putting portion 64 of an operation lever 63. Thus, the holding portion 56 can decide the position of the flexible tube 55 so that the other end of the flexible tube 55 faces in a direction in which the operation lever 63 is disposed. As shown in FIG. 3A and FIG. 3B, the holding portion 56 has a holding portion body 65, a third connection mouth ring 66 which is attached to the holding portion body 65, and a treatment instrument plug 67. The third connection mouth ring 66 has the same structure as the first connection mouth ring 27 of the endoscope 12.

The treatment instrument plug 67 similar to a publicly known forceps plug may be used in the same manner as the aforementioned assistant instrument plug 44. Thus, the treatment instrument plug 67 can prevent, by the valve structure thereof, the outside leakage of bodily fluids in the body cavity flowing backward through the treatment instrument insertion channel 15 of the endoscope 12 and the insertion path 58 of the assistant instrument 14. The treatment instrument plug 67 can also prevent the outside leakage of liquids such as bodily fluids flowing through the treatment instrument insertion channel 15 of the endoscope 12 and the insertion path 58 of the assistant instrument 14 even in a state where the insertion section 31 of the treatment instrument 13 is inserted therethrough. The treatment instrument plug 67 also serves as a brake which prevents unintentional movement of the treatment instrument 13.

The holding portion body 65 is made of, for example, a resin material. The holding portion body 65 has a base body 68 which forms the proximal end of the insertion path 58, and a pair of arms 71 extended from the base body 68. The holding portion body 65 can catch the grasping portion 42 between the arms 71 when the pair of arms 71 are elastically deformed so that the space between the arms 71 temporarily expands relative to the operation portion 16 (the grasping portion 42) indicated by a broken line. Thus, the holding portion body 65 can be easily attached to and detached from the outer surface of the grasping portion 42. The pair of arms 71 can catch not only the grasping portion 42 but also an anti-breakage 72 in which the proximal side of the insertion portion 17 is located.

As shown in FIG. 1A and FIG. 1B, the endoscope 12 further has the operation lever 63 (treatment instrument back-and-forth movement lever) which allows the position of the treatment instrument 13 in the axial direction (longitudinal direction) to be finely adjusted with the thumb of the left hand. The operation lever 63 is attached to the shaft 47 to be able to rotate around the shaft 47 to which the curving operation knobs 48A and 48B of the operation portion 16 are fixed. Thus, the operation lever 63 can rotate in a direction along the rotation direction of the curving operation knobs 48A and 48B which are the second operation levers. Therefore, the operation direction of the operation lever 63 is a direction in which the operation lever 63 can be ergonomically naturally moved with the thumb of the left hand, and the surgeon can operate the operation lever 63 without stress.

The operation lever 63 can rotate between a P position, and a Q position which is rotated a certain angle from the P position around the shaft. In the present embodiment, no torque to be rotational resistance is applied to the operation lever 63. However, for example, when the operation lever 63 is operated in a direction in which the treatment instrument 13 is sent to the outside from the treatment instrument insertion channel 15 or in a direction in which the treatment instrument 13 is returned to the treatment instrument insertion channel 15 side by resistance force applying means such as a torsion coil spring, certain rotation resistance force in a direction opposite to the rotation direction of the operation lever 63 may be applied.

Figure 4A:
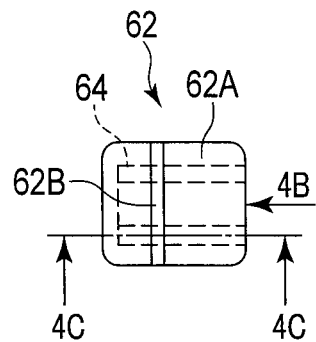
FIG. 4A is a top view showing an elastic member of an operation lever of the endoscope of the endoscopic system shown in FIG. 1 from an upper surface direction.
Figure 4B:
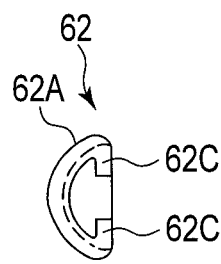
FIG. 4B is a schematic diagram showing a state where the elastic member shown in FIG. 4A is seen from the direction of an arrow 4B.
Figure 4C:
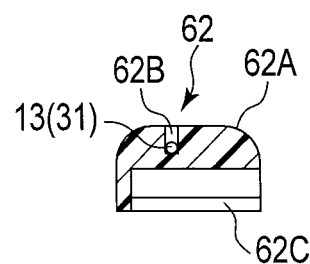
FIG. 4C is a sectional view showing the elastic member shown in FIG. 4A cut at the position of the line 4C-4C.

The operation lever 63 has a lever body 73 extending in an arm shape from the shaft 47, the finger putting portion 64 provided at the distal end of the lever body 73, and an elastic member 62 which covers the finger putting portion 64. As shown in FIG. 4A to FIG. 4C, the elastic member 62 has an elastic member body 62A, a slit 62B (slot) provided in the elastic member body 62A, and engagement portions 62C which protrude from the edges of the elastic member body 62A and thus engage with the back side of the finger putting portion 64. The elastic member 62 is removably attached to the finger putting portion 64. The elastic member 62 is integrally molded with, for example, silicone rubber.

The elastic member 62 may be formed by any other kind of resin material or rubber material which is not slippery and which is a rubber-like elastic material. The width dimension of the slit 62B is configured to be the same as or slightly smaller than the width dimension of the insertion section 31 of the treatment instrument 13. Thus, the elastic member 62 can hold the treatment instrument 13 from slipping by disposing the treatment instrument 13 within the slit 62B. The elastic member 62 is one example of a catching portion to catch the treatment instrument 13. Although one slit 62B is provided in the present embodiment, two or more slits 62B may be provided in the elastic member body 62A to move two or more treatment instruments 13 back and forth at the same time. When two or more slits 62B are provided in the elastic member body 62A, the slits 62B are preferably provided parallel to each other.

Next, functions of the endoscopic system 11 having the above configuration are described with reference to FIG. 1A and FIG. 1B. Here, a layer under an affected region S is filled with a liquid such as physiological saline, and the part around the affected region S is cut off with an electric scalpel. An example in which endoscopic submucosal dissection (ESD) is conducted is briefly described.

The surgeon grasps the grasping portion 42 of the endoscope 12 with the left hand, and grasps the outer circumferential surface of the insertion portion 17 with the right hand. The surgeon inserts the distal configuration portion 21 at the distal end of the insertion portion 17 toward the affected region S through an opening of a body cavity (lumen) T of a living tissue L while looking at an observation image which is displayed on an unshown monitor by the observation optical system of the endoscope 12. In this instance, while grasping the grasping portion 42 of the endoscope 12 with the left hand, the surgeon suitably operates the curving operation knobs 48A and 48B, and performs operations to push, pull, and twist the insertion portion 17 with the right hand. The surgeon then brings the distal configuration portion 21 of the insertion portion 17 a suitable distance closer to the affected region S.

In a state where the surgeon grasps the insertion portion 17 of the endoscope 12 with the right hand and maintains a positional relation between a distal face of the distal configuration portion 21 of the insertion portion 17 and the affected region S, an assistant (another surgeon) attaches the coupling portion 45 at the proximal end of the assistant instrument 14 to the hand-side opening 26 (first connection mouth ring 27) of the endoscope, and attaches the holding portion 56 at the distal end of the assistant instrument 14 which assists the movement of the treatment instrument to the grasping portion 42 via the arms 71. The assistant then puts the insertion section 31 of the treatment instrument 13 through the insertion path 58 of the assistant instrument 14 and the treatment instrument insertion channel 15 of the endoscope 12 to dispose the end effector 52 in the vicinity of the distal configuration portion 21 of the insertion portion 17 of the endoscope 12. The assistant further adjusts the protrusion length of the treatment instrument 13 protruding into the body cavity from the distal end of the endoscope 12 to a proper value, and then fits and sets the treatment instrument 13 (the insertion section 31) extending from the treatment instrument plug 67 in the slit 62B formed in the elastic member 62 of the operation lever 63. In the present embodiment, the catching portion is configured by the slit 62B, and it is therefore easy to attach and detach the treatment instrument 13 to and from the operation lever 63. This completes the preparation before a treatment.

The surgeon can make such a fine adjustment as to move the position of the treatment instrument 13 (the insertion section 31), for example, about ±10 mm in the axial direction by rotating the operation lever 63 around the shaft 47. That is, the surgeon can conduct such a sensitive maneuver as to perform operations to push, pull, and twist the insertion portion 17 while grasping the insertion portion 17 with the right hand, and subtly change the protrusion length of the end effector 52 of the treatment instrument 13 from the distal configuration portion 21 of the insertion portion 17 of the endoscope 12 with the thumb of the left hand grasping the operation portion 16 to perform high-frequency cutting with the treatment instrument 13 using, for example, high-frequency energy.

The assistant who is not the surgeon of the endoscope 12 generally operates the base portion 54 of the treatment instrument 13 in accordance with the surgeon's instruction. The surgeon generally starts and stops the output of the high-frequency energy by operating, for example, a foot switch.

In the ESD treatment, more than one treatment instrument 13 are replaced and used in the treatment instrument insertion channel 15 of the assistant instrument 14 which assists the movement of the treatment instrument and the endoscope 12. The replacement work is done by the assistant (another surgeon) instead of the surgeon holding the insertion portion 17 of the endoscope 12.

First, the part around the affected region S is marked by the first treatment instrument 13 (marking treatment instrument). The first treatment instrument 13 is then replaced with the second treatment instrument 13 (local injection treatment instrument) to locally inject a drug such as physiological saline into a submucosal layer of the affected region S. The second treatment instrument 13 is then further replaced with the third treatment instrument 13 (high-frequency knife) to cut open a mucous membrane around the affected region S to surround the marking with the third treatment instrument 13. The submucosal layer of the affected region S is then detached preferably by using the same third treatment instrument 13 (high-frequency knife). Bleeding in the part detached by use of, for example, high-frequency energy is then stanched, and the third treatment instrument 13 is replaced with the fourth treatment instrument 13 (e.g. grasping forceps) to collect the affected region S.

The surgeon does not take the right hand off the insertion portion 17 when twisting and turning the insertion portion 17 around its axis with the right hand. Thus, losing sight of the affected region S when marking the part around the affected region can be inhibited. It is also possible to maintain the state in which the insertion portion 17 is grasped with the right hand in the work to cut open the affected region S along the marking and in the work to detach the affected region S. The surgeon can also move the insertion section 31 back and forth in the axial direction to finely adjust cutting depth by suitably moving the operation lever 63.

The surgeon then signals the assistant to output energy, for example, when performing the work to cut open and detach the affected region S using high-frequency energy. The leakage of, for example, blood from the treatment instrument plug 67 to the outside of the assistant instrument 14 which assists the movement of the treatment instrument is inhibited by the treatment instrument plug 67 having the valve structure during the treatment. At the time of the replacement of the treatment instruments 13 or after the treatment, the assistant pulls the insertion section 31 of the treatment instrument 13 out of the treatment instrument insertion channel 15 and the insertion path 58 of the assistant instrument 14. In this instance as well, the leakage of, for example, blood is inhibited by the treatment instrument plug 67 having the valve structure. The assistant instrument 14 which assists the movement of the treatment instrument is washed, sterilized, and disinfected, and thereby reused.

According to the first embodiment, the endoscopic system 11 comprises: the endoscope 12 having the insertion portion 17 which is inserted into a lumen and which is provided with the channel to insert the treatment instrument 13 therethrough, the operation portion 16 which is connected to the insertion portion 17 and which operates the insertion portion 17, and the operation lever 63 which is provided in the operation portion 16 and which holds and moves the treatment instrument 13 to transmit force of the aforementioned operation to the treatment instrument 13; and the assistant instrument 14 which assists the movement of the treatment instrument. The assistant instrument 14 has the flexible tube 55 in which the insertion path 58 is formed to insert the treatment instrument 13 that is inserted into the channel of the insertion portion 17, the coupling portion 45 which is connected to one end of the flexible tube 55 and which is formed so that the aforementioned channel is coupled to the insertion path 58, and the holding portion 56 which is attached to the vicinity of the other end of the flexible tube 55 and which holds the operation portion 16 so that the other end of the flexible tube 55 faces toward the side where the operation lever 63 is disposed.

According to this configuration, the treatment instrument 13 can be moved back and forth by the fingers of the hand grasping the operation portion 16 because the operation lever 63 is provided in the operation portion 16. Thus, the surgeon can freely use the other hand which does not grasp the operation portion 16. Consequently, the other hand can concentrate on the back-and-forth movement and twisting operations of the insertion portion 17. Thus, the surgeon's workability can be improved. It is also possible to conduct such a complicated treatment as to change the protrusion length of the treatment instrument 13 with the hand grasping the operation portion 16 and perform cutting while twisting the insertion portion 17 with the other hand. Moreover, the loop shape of the flexible tube 55 can be set to a certain size by the coupling portion 45 and the holding portion 56, so that the operation force amount of the operation lever 63 to move the treatment instrument 13 back and forth can be always set to a certain amount and the treatment can be safely conducted.

The endoscopic system 11 comprises the curving operation knobs 48A and 48B to curving operate the insertion portion 17, and the operation lever 63 is separate from the curving operation knobs 48A and 48B. The operation lever 63 which holds the treatment instrument 13 operates to rotate around the same shaft 47 as the shaft 47 of the curving operation knobs 48A and 48B. According to these configurations, the operation lever 63 is provided on the endoscope 12 side and can therefore be disposed at an ergonomically natural position. As a result, the operation lever 63 can be easily operated with the fingers of the hand grasping the operation portion 16 of the endoscope 12, and the surgeon's workability can be improved.

The operation lever 63 is provided with the catching portion to catch the treatment instrument 13. According to this configuration, the treatment instrument 13 can be firmly caught and held in the operation lever 63. Consequently, it is possible to finely adjust the protrusion length of the treatment instrument 13 with ease by operating the operation lever 63, and improve the surgeon's workability.

The catching portion is the elastic member 62 having the slit 62B. According to this configuration, the catching portion on which the treatment instrument 13 does not easily slip can be obtained by a simple structure, and the treatment instrument 13 can be easily attached to and detached from the catching portion.

The endoscopic system 11 comprises the treatment instrument 13 which is inserted into the endoscope 12 and which is moved back and forth by the assistant instrument 14 that assists the movement of the treatment instrument, and the operation lever 63 moves the treatment instrument 13 back and forth by being operated in a state where the operation lever 63 is holding the treatment instrument 13.

According to this configuration, the surgeon can easily move the treatment instrument 13 back and forth by operating the operation lever 63, so that the surgeon's workability can be improved, and the surgeon can concentrate on surgery more.

Second Embodiment

Figure 5A:
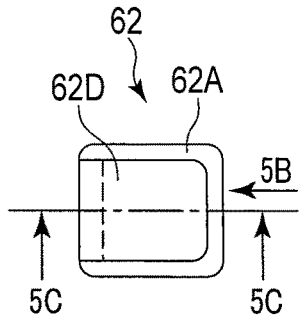
FIG. 5A is a top view showing the elastic member of the endoscopic system according to a second embodiment from an upper surface direction.
Figure 5B:
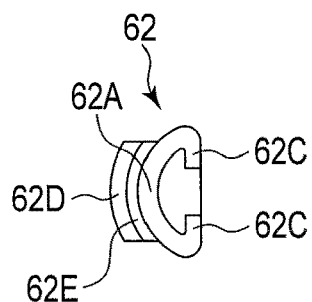
FIG. 5B is a schematic diagram showing a state where the elastic member shown in FIG. 5A is seen from the direction of an arrow 5B.
Figure 5C:
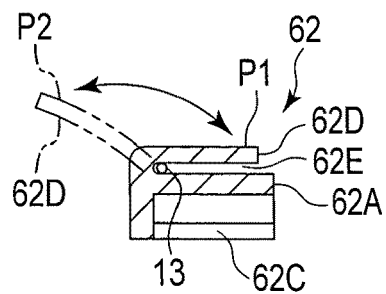
FIG. 5C is a sectional view cut at the position of the line 5C-5C in FIG. 5A.

Now, the second embodiment of the endoscopic system 11 is described with reference to FIG. 5A to FIG. 5C. The endoscopic system 11 according to the second embodiment is different from that according to the first embodiment in that the shape of the elastic member 62 of the operation lever 63 is different, but is the same as that according to the first embodiment in other parts. Therefore, parts different from those in the first embodiment are principally described below, and the same parts as those in the first embodiment are neither shown nor described.

The endoscope 12 has the operation lever 63 which can finely adjust the position of the treatment instrument 13 in the axial direction. The operation lever 63 is attached to the shaft 47 to be able to rotate around the shaft 47 to which the curving operation knobs 48A and 48B of the operation portion 16 are fixed. Although no particular resistance force is applied when the operation lever 63 is rotated in the present embodiment, certain resistance force in a direction opposite to the rotation direction may be applied to the operation lever 63 as in the first embodiment.

The operation lever 63 has the lever body 73 extending in an arm shape from the shaft 47, the finger putting portion 64 provided at the distal end of the lever body 73, and an elastic member 62 which covers the finger putting portion 64. The shapes of the lever body 73 and the finger putting portion 64 are similar to those in the first embodiment.

The elastic member 62 has the domed elastic member body 62A, a tongue 62D protruding from the outer edge of the elastic member body 62A and extending substantially parallel to the top surface of the elastic member body 62A, a clearance 62E (slit) provided between the elastic member body 62A and the tongue 62D, and the engagement portions 62C which protrude from the edges of the elastic member body 62A and thus engage with the back side of the finger putting portion 64. The elastic member 62 is integrally molded with, for example, silicone rubber, but may be made of any other material which is not slippery and which is a rubber-like elastic material. The width dimension of the clearance 62E (slit) is configured to be the same as or slightly smaller than the width dimension of the insertion section 31 of the treatment instrument 13. The elastic member 62 is one example of the catching portion.

The tongue 62D can be elastically deformed between a first position P1 at which the tongue 62D is parallel to the top surface of the elastic member body 62A, and a second position P2 at which the tongue 62D is located away from the elastic member body 62A. If the treatment instrument 13 is disposed in the clearance 62E to put the tongue 62D at the first position P1, the elastic member 62 can grip the treatment instrument 13 between the elastic member body 62A and the tongue 62D. If the surgeon holds the tongue 62D from the upper side with the fingers in this state, the treatment instrument 13 comes into close contact with the elastic member body 62A and the tongue 62D, and the treatment instrument 13 can be gripped in a less slippery state.

When the treatment instrument 13 is to be detached from the elastic member 62, it is possible to easily detach the treatment instrument 13 from the elastic member 62 by opening the tongue 62D to the second position P2.

Functions of the endoscopic system 11 according to the second embodiment are substantially similar to those according to the first embodiment. That is, in a state where the surgeon grasps the insertion portion 17 of the endoscope 12 with the right hand and maintains a positional relation between the distal face of the distal configuration portion 21 of the insertion portion 17 and the affected region S, the assistant (another surgeon) attaches the coupling portion 45 at the proximal end of the assistant instrument 14 which assists the movement of the treatment instrument to the hand-side opening 26 (first connection mouth ring 27) of the endoscope 12, and attaches the holding portion 56 at the distal end of the assistant instrument 14 which assists the movement of the treatment instrument to the grasping portion 42 via the arms 71. The assistant then puts the insertion section 31 of the treatment instrument 13 through the insertion path 58 of the assistant instrument 14 and the treatment instrument insertion channel 15 of the endoscope 12 to dispose the end effector 52 in the vicinity of the distal configuration portion 21 of the insertion portion 17 of the endoscope 12. The assistant further adjusts the protrusion length of the treatment instrument 13 protruding into the body cavity from the distal end of the endoscope 12 to a proper value, and then fits and sets the treatment instrument 13 (the insertion section 31) extending from the treatment instrument plug 67 in the clearance 62E (slit) formed in the operation lever 63. This completes the preparation before a treatment.

The surgeon can make such a fine adjustment as to move the position of the treatment instrument 13 (the insertion section 31), for example, about ±10 mm in the axial direction by rotating the operation lever 63 around the shaft 47. That is, the surgeon can conduct such a sensitive maneuver as to subtly change the protrusion length of the end effector 52 of the treatment instrument 13 from the distal configuration portion 21 of the insertion portion 17 of the endoscope 12 with the thumb of the left hand grasping the operation portion 16 while grasping the insertion portion 17 with the right hand to perform high-frequency cutting with the treatment instrument 13 using, for example, high-frequency energy.

According to the second embodiment, the operation lever 63 is pressed by the fingers from the upper side of the tongue 62D when operated, so that the treatment instrument 13 can be brought into closer contact with the elastic member 62, and the treatment instrument 13 can be less slippery on the elastic member 62 (catching portion). It is also possible to put more than one treatment instrument 13 between the tongue 62D and the elastic member body 62A. Therefore, for example, it is possible to finely adjust the positions of these treatment instruments 13 at the same time while maintaining the positional relation between these treatment instruments 13. Thus, the surgeon's workability can be improved.

Third Embodiment

Figure 6A:
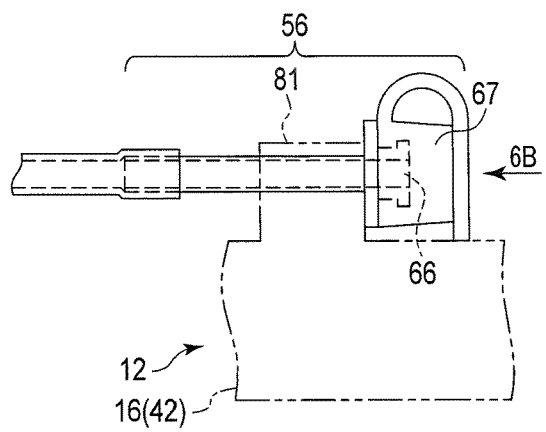
FIG. 6A is a schematic diagram showing, in a magnified form, a part of the treatment instrument back-and-forth movement assistant instrument and the operation portion of the endoscope according to the endoscopic system of the third embodiment.
Figure 6B:
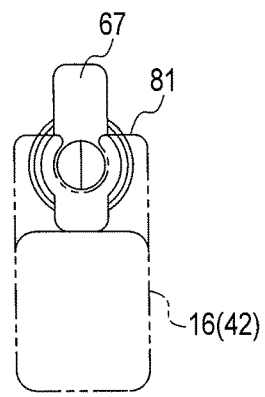
FIG. 6B is a schematic diagram showing a state where the treatment instrument back-and-forth movement assistant instrument and the operation portion shown in FIG. 6A are seen from the direction of an arrow 6B.
Figure 6C:
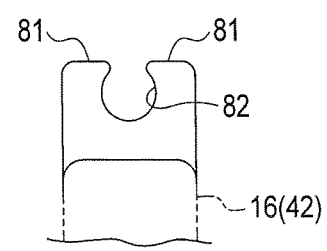
FIG. 6C is a schematic diagram showing the operation portion in a state where the treatment instrument back-and-forth movement assistant instrument shown in FIG. 6A is detached.

Now, the third embodiment of the endoscopic system 11 is described with reference to FIG. 6A to FIG. 6C. The endoscopic system 11 according to the third embodiment is different from that according to the first embodiment in that the configuration of the holding portion 56 of the assistant instrument 14 which assists the movement of the treatment instrument and the configuration of the operation portion 16 of the endoscope 12 are different, but is the same as that according to the first embodiment in other parts. Therefore, parts different from those in the first embodiment are principally described below, and the same parts as those in the first embodiment are neither shown nor described.

The holding portion 56 of the assistant instrument 14 which assists the movement of the treatment instrument is provided in the vicinity of the finger putting portion 64 of the operation lever 63 in the same manner as that shown in FIG. 1A and FIG. 1B. Thus, the holding portion 56 can decide the position of the flexible tube 55 so that the other end of the flexible tube 55 faces in a direction in which the operation lever 63 is disposed. As shown in FIG. 6A to FIG. 6C, the holding portion 56 has the tubular holding portion body 65, the third connection mouth ring 66 which is attached to the holding portion body 65, and the treatment instrument plug 67.

The holding portion body 65 is made of, for example, a resin material. The configuration of the third connection mouth ring 66 is similar to that of the first connection mouth ring 27 of the endoscope 12. The treatment instrument plug 67 similar to a publicly known forceps plug may be used in the same manner as the aforementioned assistant instrument plug 44. Thus, the treatment instrument plug 67 can prevent, by the valve structure thereof, the outside leakage of bodily fluids in the body cavity flowing backward through the treatment instrument insertion channel 15 of the endoscope 12 and the insertion path 58 of the assistant instrument 14 which assists the movement of the treatment instrument. The treatment instrument plug 67 can also prevent the outside leakage of liquids such as bodily fluids flowing through the treatment instrument insertion channel 15 of the endoscope 12 and the insertion path 58 of the assistant instrument 14 in a state where the insertion section 31 of the treatment instrument 13 is inserted therethrough.

Meanwhile, the endoscope 12 according to present embodiment has bulging portions 81 bulging in parts of the grasping portion 42 of the operation portion 16. A cutout 82 which is substantially circularly cut out is formed in the bulging portions 81. The bulging portions 81 can fit and hold the holding portion body 65 of the assistant instrument 14 in the cutout 82. The holding portion body 65 of the assistant instrument 14 which assists the movement of the treatment instrument can be fixed to the operation portion 16 or detached from the operation portion 16 via the bulging portions 81. The case 46 of the operation portion 16 is made of, for example, a resin material.

Functions of the endoscopic system 11 according to the third embodiment are substantially similar to those according to the first embodiment. That is, in a state where the surgeon grasps the insertion portion 17 of the endoscope 12 with the right hand and maintains a positional relation between the distal face of the distal configuration portion 21 of the insertion portion 17 and the affected region S, the assistant (another surgeon) attaches the coupling portion 45 at the proximal end of the assistant instrument 14 to the hand-side opening 26 (first connection mouth ring 27) of the endoscope 12, and attaches the holding portion 56 at the distal end of the assistant instrument 14 which assists the movement of the treatment instrument to the grasping portion 42 via the bulging portions 81 (the cutout 82). The assistant then puts the insertion section 31 of the treatment instrument 13 through the insertion path 58 of the assistant instrument 14 and the treatment instrument insertion channel 15 of the endoscope 12 to dispose the end effector 52 in the vicinity of the distal configuration portion 21 of the insertion portion 17 of the endoscope 12. The assistant further adjusts the protrusion length of the treatment instrument 13 protruding into the body cavity from the distal end of the endoscope 12 to a proper value, and then fits and sets the treatment instrument 13 (the insertion section 31) extending from the treatment instrument plug 67 in the slit 62B formed in the operation lever 63. This completes the preparation before a treatment.

The surgeon can make such a fine adjustment as to move the position of the treatment instrument 13 (the insertion section 31), for example, about ±10 mm in the axial direction by rotating the operation lever 63 around the shaft 47. That is, the surgeon can conduct such a sensitive maneuver as to subtly change the protrusion length of the end effector 52 of the treatment instrument 13 from the distal configuration portion 21 of the insertion portion 17 of the endoscope 12 with the thumb of the left hand grasping the operation portion 16 while grasping the insertion portion 17 with the right hand to perform high-frequency cutting with the treatment instrument 13 using, for example, high-frequency energy.

According to the third embodiment, the holding portion 56 of the assistant instrument 14 which assists the movement of the treatment instrument can be disposed on the side where the operation lever 63 is disposed. This allows the treatment instrument 13 to be smoothly moved back and forth by the operation of the operation lever 63. Because the holding portion 56 can be attachable to and detachable from the operation portion 16, the surgeon's or assistant's workability can be improved.

Fourth Embodiment

Next, the fourth embodiment of the endoscopic system 11 is described with reference to FIG. 7A and FIG. 7B. The endoscopic system 11 according to the fourth embodiment is different from that according to the first embodiment in that the configuration of the holding portion 56 of the assistant instrument 14 which assists the movement of the treatment instrument is different, but is the same as that according to the first embodiment in other parts. Therefore, parts different from those in the first embodiment are principally described below, and the same parts as those in the first embodiment are neither shown nor described.

The holding portion 56 of the assistant instrument 14 which assists the movement of the treatment instrument is provided in the vicinity of the finger putting portion 64 of the operation lever 63 in the same manner as that shown in FIG. 1A and FIG. 1B. Thus, the holding portion 56 can decide the position of the flexible tube 55 so that the other end of the flexible tube 55 faces in a direction in which the operation lever 63 is disposed. As shown in FIG. 7A and FIG. 7B, the holding portion 56 has the block-shaped holding portion body 65 having an abutment surface to abut on the operation portion 16 (the grasping portion 42), the third connection mouth ring 66 which is attached to the holding portion body 65, and the treatment instrument plug 67. The holding portion body 65 is made of, for example, a resin material. The third connection mouth ring 66 has a configuration similar to that of the first connection mouth ring 27 of the endoscope 12. The treatment instrument plug 67 similar to a publicly known forceps plug may be used in the same manner as the aforementioned assistant instrument plug 44.

The treatment instrument plug 67 is integrally formed by, for example, a resin material. The treatment instrument plug 67 has a treatment instrument plug body 67A which surrounds the third connection mouth ring 66, a lid portion 67B attachable to and detachable from the treatment instrument plug body 67A, and a string-shaped band portion 67C which couples the treatment instrument plug body 67A to the lid portion 67B. The band portion 67C can be wound around the operation portion 16 (the grasping portion 42) of the endoscope 12. The band portion 67C can fix the holding portion 56 to the operation portion 16 in a state where the band portion 67C is wound around the operation portion 16 (the grasping portion 42) of the endoscope 12.

The treatment instrument plug 67 can prevent, by the valve structure thereof, the outside leakage of bodily fluids in the body cavity flowing backward through the treatment instrument insertion channel 15 of the endoscope 12 and the insertion path 58 of the assistant instrument 14 which assists the movement of the treatment instrument. The treatment instrument plug 67 can also prevent the outside leakage of liquids such as bodily fluids flowing through the treatment instrument insertion channel 15 of the endoscope 12 and the insertion path 58 of the assistant instrument 14 which assists the movement of the treatment instrument in a state where the insertion section 31 of the treatment instrument 13 is inserted therethrough.

Functions of the endoscopic system 11 according to the fourth embodiment are substantially similar to those according to the first embodiment. That is, in a state where the surgeon grasps the insertion portion 17 of the endoscope 12 with the right hand and maintains a positional relation between the distal face of the distal configuration portion 21 of the insertion portion 17 and the affected region S, the assistant (another surgeon) attaches the coupling portion 45 at the proximal end of the assistant instrument 14 to the hand-side opening 26 (first connection mouth ring 27) of the endoscope 12, and attaches the holding portion 56 at the distal end of the assistant instrument 14 which assists the movement of the treatment instrument to the grasping portion 42 via the band portion 67C.

The assistant then puts the insertion section 31 of the treatment instrument 13 through the insertion path 58 of the assistant instrument 14 and the treatment instrument insertion channel 15 of the endoscope 12 to dispose the end effector 52 in the vicinity of the distal configuration portion 21 of the insertion portion 17 of the endoscope 12. The assistant further adjusts the protrusion length of the treatment instrument 13 protruding into the body cavity from the distal end of the endoscope 12 to a proper value, and then fits and sets the treatment instrument 13 (the insertion section 31) extending from the treatment instrument plug 67 in the slit 62B formed in the operation lever 63. This completes the preparation before a treatment.

The surgeon can make such a fine adjustment as to move the position of the treatment instrument 13 (the insertion section 31), for example, about ±10 mm in the axial direction by rotating the operation lever 63 around the shaft 47. That is, the surgeon can conduct such a sensitive maneuver as to subtly change the protrusion length of the end effector 52 of the treatment instrument 13 from the distal configuration portion 21 of the insertion portion 17 of the endoscope 12 with the thumb of the left hand grasping the operation portion 16 while grasping the insertion portion 17 with the right hand to perform high-frequency cutting with the treatment instrument 13 using, for example, high-frequency energy.

According to the fourth embodiment, the holding portion 56 of the assistant instrument 14 which assists the movement of the treatment instrument can be disposed on the side where the operation lever 63 is disposed. This allows the treatment instrument 13 to be smoothly moved back and forth by the operation of the operation lever 63. Because the holding portion 56 can be attachable to and detachable from the operation portion 16, the surgeon's or assistant's workability can be improved.

While several embodiments have been specifically described so far with reference to the drawings, this invention is not limited to the embodiments described above, and includes all embodiments that are implemented without departing from the spirit of the invention. The configurations included in any of the embodiments described above can be combined to configure one endoscopic system.

The present invention is intended to provide an endoscopic system having an assistant instrument which assists the movement of a treatment instrument that is satisfactory in workability.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An endoscopic system comprising:
an endoscope comprising:
an insertion portion configured to be inserted into a body, the insertion portion having a channel to insert a treatment instrument through the channel, and
an operation portion connected to the insertion portion, the operation portion including a grasping portion configured to be grasped by a surgeon and an operation lever rotatably provided in the operation portion, the operation lever including a catching portion that catches the treatment instrument, the operation lever being configured to move the treatment instrument while being held by the catching portion to transmit a force of operation by the surgeon to the treatment instrument; and
an assistant instrument which assists the movement of the treatment instrument, the assistant instrument comprising:
a flexible tube in which an insertion path is formed to insert the treatment instrument,
a coupling portion which connects one end of the flexible tube and the channel so that the channel communicates with the insertion path, and
a holding portion including a base body connected to an other end of the flexible tube, the holding portion further including an attachment instrument attached to the operation portion so that the base body is disposed on a side of the operation portion where the operation lever is disposed.

2. The endoscopic system according to claim 1,
the operation portion further comprises a curving operation knob to operate the insertion portion,
wherein the operation lever is separate from the curving operation knob.

3. The endoscopic system according to claim 2, wherein the operation lever which holds the treatment instrument operates to rotate around the same shaft as a shaft of the curving operation knob.

4. The endoscopic system according to claim 1, wherein the catching portion is an elastic member comprising a slit.

5. The endoscopic system according to claim 1,
wherein the operation lever is operated in a state where the treatment instrument that is inserted into the endoscope is held by the catching portion, thereby moving the treatment instrument back and forth.

6. The endoscopic system according to claim 1, wherein the attachment instrument includes one of an arm that catches and detachably attaches to the operation portion, or a band that is wound around and detachably attaches to the operation portion.

\* \* \* \* \*